United States Patent [19]
Spotorno et al.

[11] Patent Number: 4,834,759
[45] Date of Patent: May 30, 1989

[54] ENDOPROSTHESIS FOR A HIP JOINT

[75] Inventors: Lorenzo Spotorno, Ospedale Riuniti, Italy; Otto Frey, Winterthur, Switzerland

[73] Assignees: Sulzer Brothers Ltd., Wintherthur; Protek AG, Berne, both of Switzerland

[21] Appl. No.: 36,587

[22] Filed: Apr. 10, 1987

[30] Foreign Application Priority Data

Apr. 15, 1986 [CH] Switzerland .......................... 1489/86

[51] Int. Cl.$^4$ ............................................... A61F 2/34
[52] U.S. Cl. ..................................................... 623/22
[58] Field of Search ..................................... 623/16–23

[56] References Cited
U.S. PATENT DOCUMENTS 3,820,167 6/1974 Sivash .................................... 623/22
4,662,891 5/1987 Noiles ................................... 623/16

FOREIGN PATENT DOCUMENTS 0169978 2/1986 European Pat. Off. ............. 623/22
83/02555 8/1983 PCT Int'l Appl. .................... 623/22

Primary Examiner—Richard J. Apley
Assistant Examiner—David J. Isabella
Attorney, Agent, or Firm—Kenyon & Kenyon

[57] ABSTRACT

The external bowl of the hip joint endoprosthesis is provided with a plurality of circumferential rows of projections. In addition, each projection is provided with a flank in a plane perpendicular to the axis of symmetry of the bowl and a second flank which faces the equatorial plane of the bowl which defines an angle of from 15° to 45° with the other flank. Upon penetration into bone tissue, the flanks displace and condense the tissue to approximately the same extent so that the axial force components acting on the flanks are approximately equal. This reduces the tendency of the endoprosthesis to be expelled from the bone.

15 Claims, 1 Drawing Sheet

ENDOPROSTHESIS FOR A HIP JOINT

This invention relates to an endoprosthesis for a hip joint.

Heretofore, many types of endoprostheses have been known for use in a hip joint. In some cases, the endoprostheses have been made for cement-free anchoring in a bone and have been formed of an inner acetabular body and an external bowl in which the acetabular body is fitted and held in place by a locking structure. In addition, it has been known to shape the external bowl in a hemispherical shape and to provide the bowl of meridian slits in order to define circumferentially disposed flaps. Still further, it has been known to provide a plurality of projections, for example, in circumferential rows over the outside surface of the bowl for bone penetration.

A prosthesis of the above type is described in European Pat. No. A-0169978. In order to anchor the prosthesis in a hip bone, the external bowl is initially pressed together elastically with a tool and then set into a surgically prepared recess in the hip bone in the direction of the axis of the bowl. After removal of the tool, the acetabular body is driven into the bowl. At this time, the bowl becomes expanded and the projections on the bowl penetrate into the bone tissue forming the wall of the recess. In addition, the individual flaps of the bowl pivot about their respective bases on a circular arc so as to penetrate into the tissue. Generally, the projections are in the form of spikes which are directed radially and symmetrically of their respective axes. However, because of the axial force components which act on the spikes parallel to the axis of symmetry of the spikes, the external bowl is biased out of the bone. Further, the spongiosa, as a practical matter, is not compressed by the flanks of the spikes so that the grip of the external bowl and, thus, the prosthesis, is diminished.

Accordingly, it is an object of the invention to improve the gripping characteristics of an endoprosthesis for a hip joint.

It is another object of the invention to provide a relatively simple surface structure for fixing an acetabular-receiving bowl in a hip bone.

Briefly, the invention provides a bowl for a hip joint endoprosthesis which includes a body of generally hemispherical shape having a plurality of meridian slits defining a plurality of circumferentially disposed flaps which extend to an equatorial plane radially of a longitudinal axis. In addition, a plurality of outwardly directed projections are provided on at least some of the flaps for projecting into spongiosa. Further, at least some of the projections have a first flank disposed on a plane perpendicular to the longitudinal axis of the body and a second flank facing the equatorial plane which defines an angle of from 15° to 45° with the first flank.

Because of the form of the projections, the tip of each projection lies at least approximately in the center of a "densification band" of the spongiosa defined by the flank form and the thickness of the projection at the base. The axial forces acting upon the flank facing the equatorial plane and the opposite flank compensate each other at least approximately. Hence, biasing of the bowl out of a bone by a strongly predominating axial force in the direction of the equatorial plane is avoided.

The projections on the exterior surface of the bowl are disposed in a plurality of circumferential rows on the flaps. Further, in order to take into account the different "radii of expansion" for the individual peripheral rows of projections, the flanks of the projections of each row define a different angle from the flanks of the projections of the remaining rows. For example, the flanks of the rows define increasing angles in the direction extending away from the equatorial plane. That is, the projections in the rows closer to the pole of the bowl have greater flank angles than the rows closer to the equatorial plane.

In order to simplify production of the bowl which is preferrably made of a metal used in implant technology, the projections of each row have a tip disposed on a common jacket line with the remainder of the projections of the row. In addition, a concave circular surface is formed between each adjacent pair of projections in each row. In this way, the projections can be produced by a simple mill cutting along the jacket lines of the external form of the bowl.

In order to complete the endoprosthesis, an acetabular body is provided having a conical jacket which is sized to be received within the bowl in locked relation. To this end, each of the acetabular body and the bowl is provided with a suitable means for locking engagement with each other. For example, the bowl may be provided with an internal thread while the acetabular body is provided with an external thread by which the body can be screwed into the bowl.

These and other objects and advantages of the invention will become more apparent from the following detailed description taken in conjunction with the accompanying drawings wherein.

Figure 1:
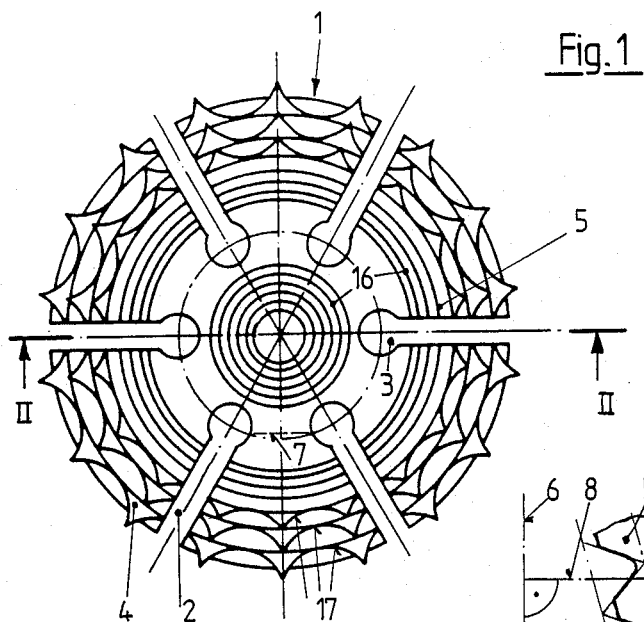
FIG. 1 illustrates a plan view of a bowl constructed in accordance with the invention.
Figure 2:
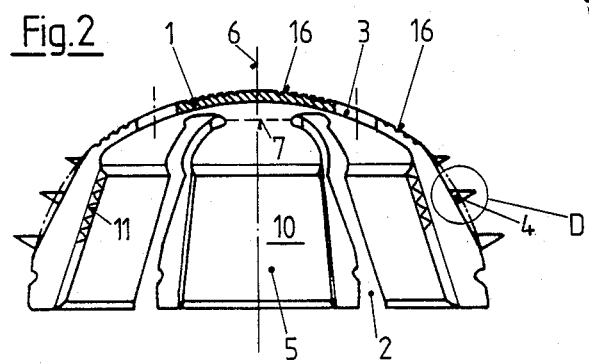
FIG. 2 illustrates a view taken on line II—II of FIG. 1.

Referring to FIGS. 1 and 2, the bowl 1 for a hip joint prosthesis includes a body of generally hemispherical shape having a plurality of meridian slits 2 which are equally distributed over the circumference of the bodyy to define a plurality of circumferentially disposed flaps 5. As indicated in FIG. 1, the slits 2 are disposed radially of a longitudinal axis 6 of the bowl 1 and terminate short of the pole of the bowl 1 in circular enlargements 3. Each flap 5 extends from a base between two adjacent enlargements 3 to the equatorial plane of the bowl 1. In this respect, as indicated in FIG. 2, the flaps 5 have flat end surfaces which together define the equatorial plane of the bowl 1.

As indicated in FIG. 1, the "maximum flap constriction" of each flap 5 extends in the area between two enlargements 3 such that a "rotational axis" 7 is situated in this region. As also indicated in FIG. 1, the centers of the circular enlargements 3 are located at approximately 65° geographical latitude.

Figure 4:
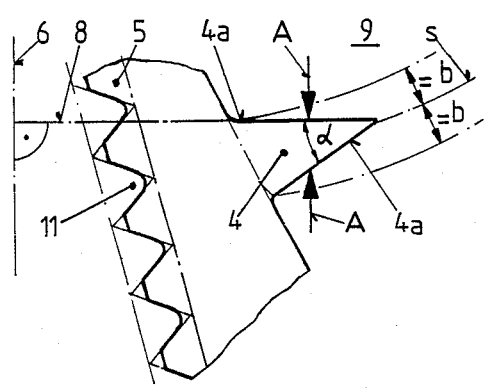
FIG. 4 illustrates an enlarged view of a projection formed in accordance with the invention.

The bowl 1 is also provided with a plurality of outwardly directed discrete projections 4 in the form of spikes which are circumferentially spaced on each of the flaps 5 for penetrating into spongiosa. As indicated in FIG. 4, each projection 4 has an upper flank 4a, as viewed, which is disposed on a plane 8 perpendicular to the longitudinal axis 6 of the bowl and a second lower flank 4a which faces the equatorial plane and defines an angle α of from 15° to 45° with the upper flank. Each projection 4 also has a tip or apex which is to penetrate into bone tissue 9 when in use.

Referring to FIGS. 1 and 2, the projections 4 are disposed in a plurality of circumferential rows 17 on the flaps 5 of the bowl 1 with the tips of the projections 4 of each row 17 disposed on a common jacket line, i.e. imaginary cylinder. As indicated in FIG. 1, the tips of the projections 4 of each row are disposed on imaginary cylinders of different diameters. In this way, the projections 4 can be readily produced, for example by a mill cutter. Further, as indicated in FIG. 1, the flaps 5 are formed with a concave circular surface between each adjacent pair of projections 4. Again, the surfaces may be form by a mill cutter in known fashion.

As indicated in FIG. 1, the external surface of the pole area of the bowl 1 is provided with a plurality of circular grooves 15 in order to increase the area of accretion for the ingrowth of issue. Also, as indicated in FIG. 2, the bowl 1 has an internal hollow cavity 10 which is shaped essentially as a truncated cone limited on one side by a bore. In addition, the interior surface of the bowl 1 is provided with a means such as a thread 11 which extends in a dis-continuous manner across the flaps 5.

Figure 3:
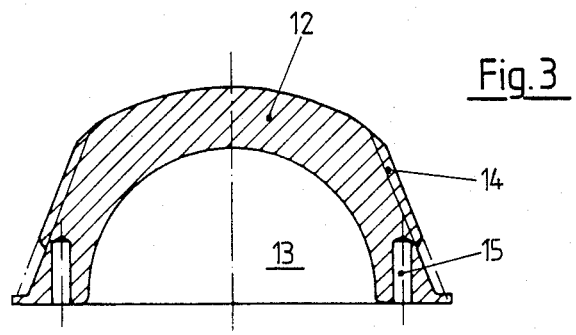
FIG. 3 illustrates a cross sectional view of an acetabular body in accordance with the invention.

Referring to FIG. 3, the endoprosthesis also has an acetabular body 12 having a conical jacket which is to be received within the bowl 1. As shown, the acetubular body 12 has an acetabular cavity 13 for receiving a spherical joint head (not shown) as well as a means in the form of a counter-thread 14 for threading into the thread 11 of the bowl. In addition, suitable bores 15 are provided at the margin of the acetabular body 12 to serve for the insertion of an appropriate screwing tool.

On threading the acetabular body 12 into the external bowl 1 via the threads 11, 14, the acetabular body 12 comes into locking engagement with the bowl 1. At the same time, the acetabular body 12 is sized to exert a radially directed expansion force on the flaps 5 so that the flaps 5 are biased outwardly into the hip bone. This, in turn, causes the projections 4 to penetrate the tissue 9 and thus become anchored in the bone.

As indicated in FIG. 4, during expansion of the bowl 1, each projection 4 penetrates into the tissue 9 while displacing and condensing the tissue at least approximately to the same extent at both flanks 4a. In this way, the areas of densification b and, thus, the axial force components A on both sides of the path s of the projection tip become at least approximately equal. Hence, the axial force components A cancel each other at least approximately. Thus, any force which would otherwise bias a flap 5 and thus the bowl 1 out of the bone is substantially reduced while at the same time, the gripping of the bowl 1 in the bone is increased.

The invention thus provides an endoprosthesis which can be anchored in a hip bone in a cement-free manner via a relatively simple expansion of the split external bowl. Further, shape and positioning of the flanks of the projections on the external bowl reduce the effect of any forces which would tend to bias the endoprosthesis out of the bone.

What is claimed is:

1. An endoprothesis for a hip joint comprising
a bowl of generally hemispherical shape having a plurality of meridian slits defining a plurality of circumferentially disposed flaps extending to an equatorial plane radially of a longitudinal axis, at least some of said flaps having a plurality of outwardly directed circumferentially spaced discrete projections thereon, each said projection having a first flank disposed on a plane perpendicular to said longitudinal axis and a second flank facing said equatorial plane and defining an angle of from 15° to 45° with said first flank; and
an acetabular body having a conical jacket received within said bowl in locked relation.

2. An endoprosthesis as set forth in claim 1 which further includes a first means on said bowl for locking engagement with a second means on said jacket.

3. An endoprosthesis as set forth in claim 1 wherein said projections are disposed in a plurality of circumferential rows on said flaps.

4. An endoprosthesis as set forth in claim 3 wherein said projections of each row each have a tip disposed on a common imaginary cylinder with the remainder of said projections of said row.

5. An endoprosthesis as set forth in claim 4 wherein each flap has a concave circular surface between each adjacent pair of projections thereon.

6. An endoprosthesis as set forth in claim 3 wherein each flap has a concave circular surface between each adjacent pair of projections thereon.

7. An endoprosthesis as set forth in claim 3 wherein said flanks of said projections of each row define a different angle from said flanks of said projections of the remaining rows.

8. An endoprosthesis as set forth in claim 7 wherein said flanks of said profections of each row define increasing flank angles in a direction extending away from said equatorial plane.

9. A bowl for a hip joint endprosthesis comprising
a body of generally hemispherical shape having a plurality of meridian slits defining a plurality of circumferentially disposed flaps extending to an equatorial plane radially of a longitudinal axis; and
a plurality of outwardly directed circumferentially spaced projections on at least some of said flaps for penetrating into spongiosa, at least some of said projections having a first flank disposed on a plane perpendicular to said longitudinal axis and a second flank facing said equatorial plane and a defining an angle of from 15° to 45° with said first flank.

10. A bowl as set forth in claim 9 which further comprises means on an interior surface of said bowl for engaging a conical jacket of an acetabular body.

11. A bowl as set forth in claim 10 wherein said means includes a plurality of threads.

12. A bowl as set forth in claim 9 wherein said projections are disposed in a plurality of circumferential rows on said flaps.

13. A bowl as set forth in claim 12 wherein said projections of each row each have a tip disposed on a common imaginary cylinder with the remainder of said projections of said row.

14. A bowl as set forth in claim 13 wherein each flap has a concave circular surface between each adjacent pair of projections thereon.

15. A bowl as set forth in claim 12 wherein said flanks of said projections of each row define an angle of increasing size in a direction extending away from said equatorial plane.

* * * * *